US00PP11333P

United States Patent [19]

Turc

[11] Patent Number: Plant 11,333

[45] Date of Patent: Apr. 4, 2000

[54] ALSTROEMERIA PLANT NAMED 'LOIRIDAU'

[75] Inventor: Jean Pierre Turc, Mazé , France

[73] Assignee: Selection New Plant SARL, Le Luc, France

[21] Appl. No.: 09/116,953

[22] Filed: Jul. 17, 1998

[51] Int. Cl.[7] ..... A01H 5/00

[52] U.S. Cl. ..... Plt./309

[58] Field of Search ..... Plt./309

*Primary Examiner*—Howard J. Locker

*Attorney, Agent, or Firm*—Burns, Doane, Swecker & Mathis, L.L.P.

[57] ABSTRACT

A new and distinct variety of Alstroemeria plant of very tall height is provided which abundantly forms on a substantially continuous basis attractive large pink flowers (as illustrated). The flowers are borne on peduncles as an umbel. The plant propagates well by the division of roots. The plant can be grown as distinctive ornamentation under mild temperature conditions.

1 Drawing Sheet

SUMMARY OF THE INVENTION

The new variety of Alstroemeria was created by artificial pollination wherein two parents were crossed which previously had been studied in the hope that they would contribute the desired characteristics. The female parent (i.e., the seed parent) of the new variety was the 'Turcalva' variety (non-patented in the United States). The 'Turcalva' variety is marketed in Europe under the VALERIE trademark. The male parent (i.e., the pollen parent) of the new variety was the 'Aurantiaca Rouge' variety (non-patented in the United States). The parentage of the new variety can be summarized as follows:

'Turcalva'×'Aurantiaca Rouge'.

The seeds resulting from the above pollination were sown and small plants were obtained which were physically and biologically different from each other. Selective study resulted in the identification of a single plant of the new variety.

It was found that the new Alstroemeria plant of the present invention possesses the following combination of characteristics:

(a) forms in abundance attractive large pink flowers on peduncles as an umbel,
(b) exhibits a very tall plant height,
(c) propagates well by the division of roots, and
(d) is particularly suited for growing as a distinctive ornamental plant under mild temperature conditions.

The pink flowers (as illustrated) of the new variety of the present invention can be readily distinguished from the bright red flowers of the 'Loiricha' variety (U.S. Plant. Pat. No. 10,312), and the salmon pink blended with yellow flowers of the 'Loirieon' variety (U.S. Plant patent application Ser. No. 09/116,952, filed concurrently herewith).

The new variety well meets the needs of the horticultural industry. It is particularly well-suited for use as attractive ornamentation in the landscape or for growing as a decorative pot plant.

The new variety has been found to undergo asexual propagation in France by the separation or splitting of roots. Asexual propagation by the above-mentioned methods as performed in France has shown that the characteristics of the new variety are strictly transmissible from one generation to another.

The new variety has been named the 'Loiridau' variety.

BRIEF DESCRIPTION OF THE PHOTOGRAPH

The accompanying photograph shows as nearly true as it is reasonably possible to make the same, in a color illustration of this character, typical specimens of the plant parts of the new variety. The Alstroemeria plants of the new variety were sixteen months of age and were observed during June while growing in greenhouses at Mazé, Maine et Loire, France. Size information in centimeters is provided at the bottom of the photograph.

DETAILED DESCRIPTION

Figures 1, 2, 3, 4, 5, 6, 7, 8, 9, 10, 11, 12, 13, 14:
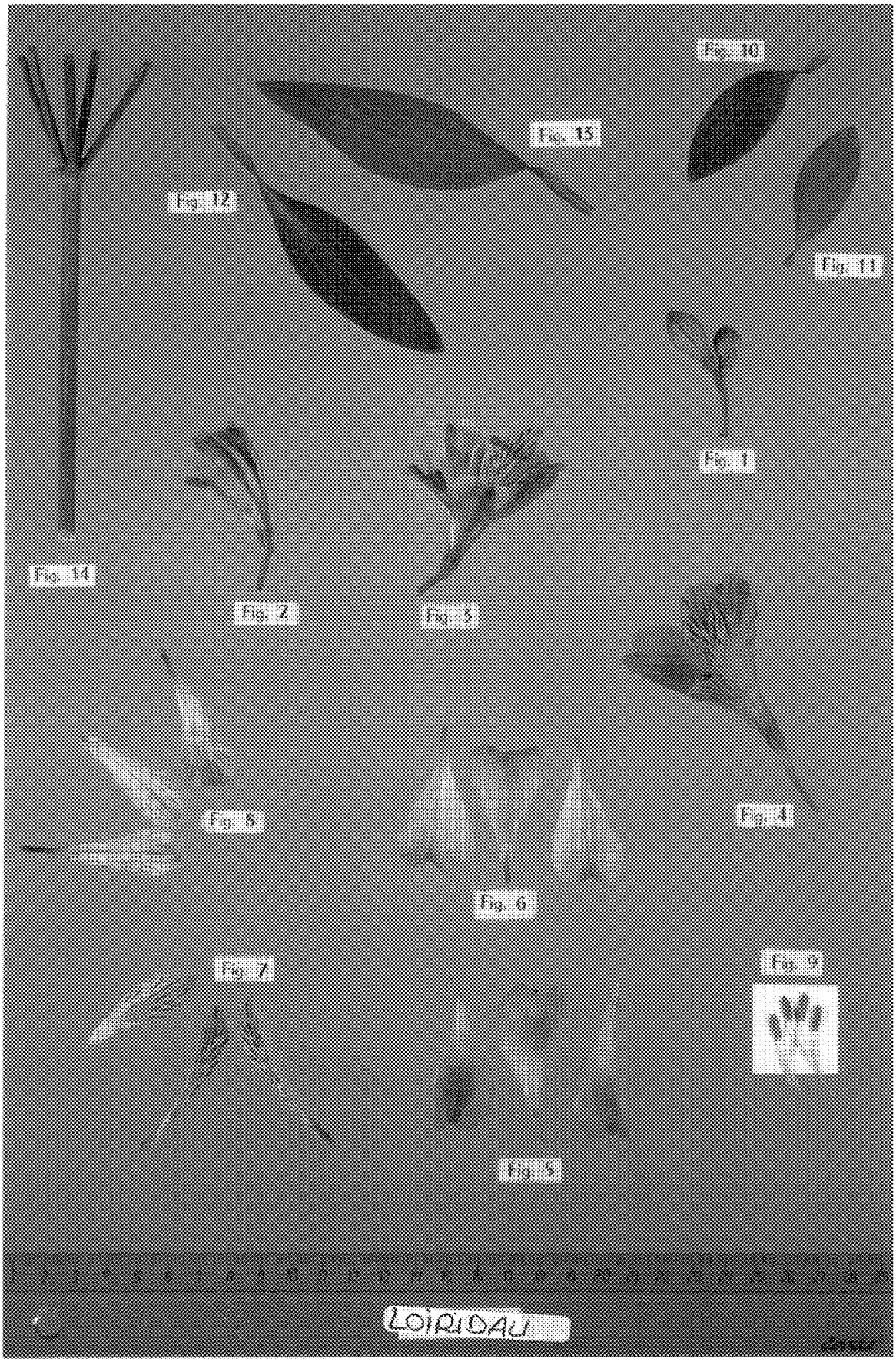
FIG. 1 illustrates specimens of two floral buds.
FIG. 2 illustrates a specimen of a floral bud in the course of opening.
FIG. 3 illustrates a specimen of a flower in the course of opening.
FIG. 4 illustrates a specimen of an open flower.
FIG. 5 illustrates specimens of external floral petals — plan view — obverse.
FIG. 6 illustrates specimens of external floral petals — plan view — reverse.
FIG. 7 illustrates specimens of central floral petals — plan view — obverse.
FIG. 8 illustrates specimens of central floral petals — plan view — reverse.
FIG. 9 illustrates specimens of stamens.
FIG. 10 illustrates a specimen of a bract — plan view — obverse.
FIG. 11 illustrates a specimen of a bract — plan view — reverse.
FIG. 12 illustrates a specimen of a leaf — plan view — obverse.
FIG. 13 illustrates a specimen of a leaf — plan view — reverse.
FIG. 14 illustrates a specimen of a stem.

The chart used in the identification of the colors is that of The Royal Horticultural Society (R.H.S. Colour Chart). Color terminology is used in some instances to indicate the corresponding colors in more common terms that are to be accorded their ordinary dictionary significance. The description is based on the observation of sixteen month-old specimens of the new variety during May while growing in greenhouses at Mazé, Maine et Loire, France.

Origin: Artificial pollination.

Parentage:

*Female.*—'Turcalva' which is marketed under the VALERIE trademark in Europe.

*Male.*—'Aurantiaca Rouge'.

Classification: Alstreomeria Hybrid.

Plant:

*Form.*—Herbaceous perennial.

*Height.*—Size: very tall, approximately 1.5 to 1.9 m. on average.

*Habit.*—Fast growing with vigorous upright stems of good strength.

*Rhizome color.*—Milky white, near White Group 155A.

*Rhizome size.*—Variable with the growing season which occurs from spring to autumn. During June a typical length is approximately 15 to 20 cm. The growth is substantially horizontal.

Foliage:

*Leaf shape.*—Elliptical.

*Leaf size.*—Approximately 14 cm. in length and approximately 3.5 cm. in width.

*Texture.*—Glossy on upper surface.

*Margin.*—Smooth.

*Color.*—Adult foliage is dark green, Yellow-Green Group 147A on the upper surface, and medium green, Green Group 137B on the under surface.

Inflorescence:

*Main stem length.*—Approximately 0.7 to 1.1 m.

*Main stem color.*—Green Group 143C.

*Peduncle length.*—Commonly approximately 10 cm.

*Peduncle disposition.*—Erect and upright.

*Peduncle color.*—Yellow-Green Group 144B.

*Buds.*—Shape: pear-shaped with a fringed base. Size: approximately 4.2 cm. in length, and approximately 1.5 cm. in diameter.

*Color.*—Yellow-Green Group 144B.

*Blooming habit.*—Continuous with no substantial interruption.

*Blooms.*—Size: large in an umbel. Diameter: approximately 6.5 cm. Depth: approximately 4.5 cm. Borne: singly on a stem, and approximately 4 to 5 blooms on average per umbel.

*Umbel size.*—Commonly approximately 12 cm. on average. Form: cup-shaped. Number of tepals: Three internal tepals and three external tepals. Arrangement: generally two concentric circles of three tepals each. Texture: soft. Appearance: satiny. Color (in course of opening): Central tepals (obverse): near Red Group 54B and lightly suffused with near Green-Yellow Group 1B at the tip, near Green-Yellow Group 1B towards the center which commonly is lighter on one tepal, and at the base an area that is near Red Group 56D. Discontinuous dark striations of Greyed-Purple Group 187B are present (as illustrated). Central tepals (reverse): Red-Purple Group 63B and lightly suffused with near Green-Yellow Group 1B at the tip, near Green-Yellow Group 1B towards the center which commonly is lighter on one tepal, and at the base near Red-Purple Group 63B towards the center and Red Group 56D on the sides suffused with Red-Purple Group 63B. External tepals (obverse): near Red Group 55B at the tip, and Red Group 55C at the base and suffused with near Red Group 54A at the outer approximately one-third of the tepal. The green-yellow coloration of the inner tepals commonly is lacking on the external tepals. External tepals (reverse): near Red Group 53D towards the center, and on the outer approximately two-thirds of the tepal Red-Purple Group 62B and lightly suffused with Red Group 53D. Darker veinlets are visible. The green-yellow coloration of the inner tepals commonly is lacking. Color (after full bloom): whitening tends to occur. Internal tepal shape: elliptic with smooth margin. External tepal shape: cordate and oblong with smooth margin. Lasting quality: approximately 4 to 5 weeks on the plant, and approximately 3 weeks when the blossoms are cut and are placed in a vase. Fragrance: none. Stamens: commonly six in number with one being arranged opposite each tepal. Anthers: before dehiscence light khaki green and after dehiscence dark khaki green in coloration, and commonly approximately 8 mm. in length. Filaments: pinkish in coloration and approximately 2.5 to 3 cm. in length. Pollen: mustard yellow in coloration. Pistils: commonly one. Styles: pinkish in coloration with a white base and approximately 3.2 cm. in length. Stigmas: pinkish-white in coloration and spotted. Fruit: greenish-brown in coloration at maturity, rounded, and commonly infertile.

Development:

*Propagation.*—Propagates well through the division of roots.

*Resistance to diseases.*—Good with respect to traditional diseases under greenhouse growing conditions.

*Resistance to frost.*—None with the best culture conditions being exhibited above 20° C.

I claim:

1. A new and distinct variety of Alstroemeria plant characterized by the following combination of characteristics:

(a) forms in abundance attractive large pink flowers on peduncles as an umbel;
(b) exhibits a very tall plant height;
(c) propagates well by the division of roots; and
(d) is particulary suited for growing as a distinctive ornamental plant under mild termperature conditions;

substantially as herein shown and described.

* * * * *

LOIRIDAU